US012478766B2

(12) United States Patent
Fukami

(10) Patent No.: US 12,478,766 B2
(45) Date of Patent: Nov. 25, 2025

(54) INSERTER, MEDICAL ELONGATED BODY SET THAT INCLUDES INSERTER, AND METHOD OF USING INSERTER

(71) Applicant: TERUMO KABUSHIKI KAISHA, Tokyo (JP)

(72) Inventor: Kazunari Fukami, Kawasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1033 days.

(21) Appl. No.: 17/405,214

(22) Filed: Aug. 18, 2021

(65) Prior Publication Data

US 2021/0379342 A1 Dec. 9, 2021

Related U.S. Application Data

(63) Continuation of application No. PCT/JP2020/003455, filed on Jan. 30, 2020.

(30) Foreign Application Priority Data

Feb. 18, 2019 (JP) ................................ 2019-026188

(51) Int. Cl.
*A61M 25/09* (2006.01)
*A61M 25/00* (2006.01)
(Continued)

(52) U.S. Cl.
CPC .. *A61M 25/09041* (2013.01); *A61M 25/0097* (2013.01); *A61M 25/0618* (2013.01); *A61M 29/00* (2013.01)

(58) Field of Classification Search
CPC ........ A61M 25/0111; A61M 25/09041; A61M 39/16; A61M 39/18
See application file for complete search history.

(56) References Cited

U.S. PATENT DOCUMENTS 5,273,052 A * 12/1993 Kraus ................. A61M 25/104 600/585
5,320,613 A 6/1994 Houge et al.
(Continued)

FOREIGN PATENT DOCUMENTS

JP H10295821 A 11/1998
JP 2004290395 A 10/2004
(Continued)

OTHER PUBLICATIONS

English translation of WO 2006/025370 A1. (Year: 2006).*
(Continued)

*Primary Examiner* — Kami A Bosworth
(74) *Attorney, Agent, or Firm* — BUCHANAN INGERSOLL & ROONEY PC

(57) ABSTRACT

An inserter, a medical elongated body set, and a method of using the inserter to effectively remove air remaining inside a distal portion of a medical elongated body of the medical elongated body set by effectively performing priming on the distal portion of the medical elongated body. The inserter assists the medical elongated body to be inserted into a medical device. The inserter includes a tubular portion having a proximal opening portion into which the medical elongated body is inserted and a distal opening portion that guides the medical elongated body to the medical device. The inserter has a main lumen through which the proximal opening portion and the distal opening portion communicate with each other. The inserter has a connector that communicates with the main lumen of the tubular portion, and connects to a liquid injection tool.

20 Claims, 5 Drawing Sheets

(51) Int. Cl.
*A61M 25/06* (2006.01)
*A61M 29/00* (2006.01)

(56) References Cited

U.S. PATENT DOCUMENTS

| | | | |
|---|---|---|---|
| 6,059,484 | A | 5/2000 | Greive |
| 2004/0147908 | A1 | 7/2004 | Duffy |
| 2005/0197663 | A1 | 9/2005 | Soma et al. |
| 2015/0306356 | A1 | 10/2015 | Gill |
| 2020/0023168 | A1 | 1/2020 | Hayakawa et al. |

FOREIGN PATENT DOCUMENTS

| | | | |
|---|---|---|---|
| JP | 2005245514 | A | 9/2005 |
| JP | 2007-000209 | A | 1/2007 |
| JP | 2008049017 | A | 3/2008 |
| WO | 97/18850 | A1 | 5/1997 |
| WO | 00/69500 | A1 | 11/2000 |
| WO | 2006/025370 | A1 | 3/2006 |
| WO | 2017/011165 | A1 | 1/2017 |
| WO | 2017/033182 | A1 | 3/2017 |
| WO | 2018/163899 | A1 | 9/2018 |
| WO | 2018181520 | A1 | 10/2018 |

OTHER PUBLICATIONS

International Search Report (PCT/ISA/210) with translation and Written Opinion (PCT/ISA/237) mailed on Mar. 24, 2020, by the Japanese Patent Office as the International Searching Authority for International Application No. PCT/JP2020/003455.

The extended European Search Report issued Mar. 2, 2022, by the European Patent Office in corresponding European Patent Application No. 20760257.4-1132. (12 pages).

English Translations of the International Search Report (Form PCT/ISA/210) and the Written Opinion of the International Searching Authority (Form PCT/ISA/237) issued on Mar. 24, 2020, by the Japanese Patent Office in corresponding International Application No. PCT/JP2020/003455. (11 pages).

* cited by examiner

FIG. 6A
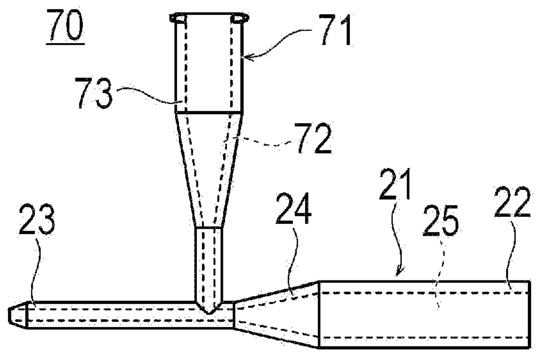
FIG. 6B
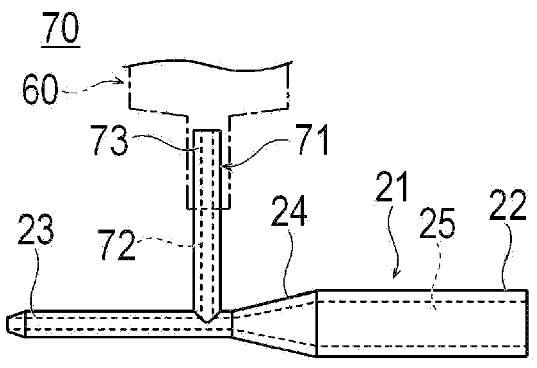
FIG. 7A
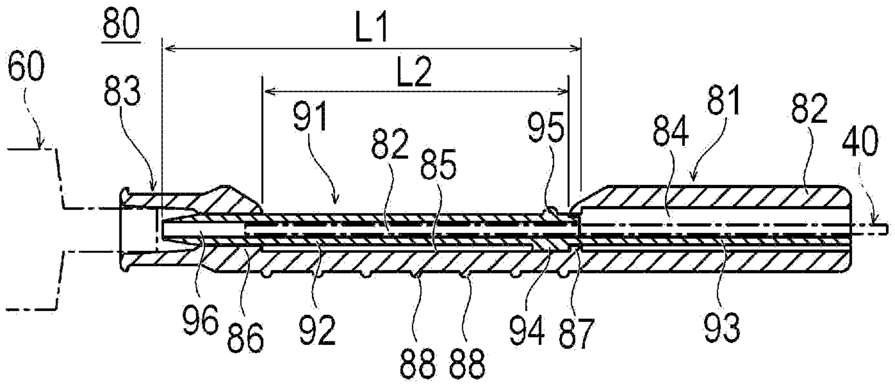
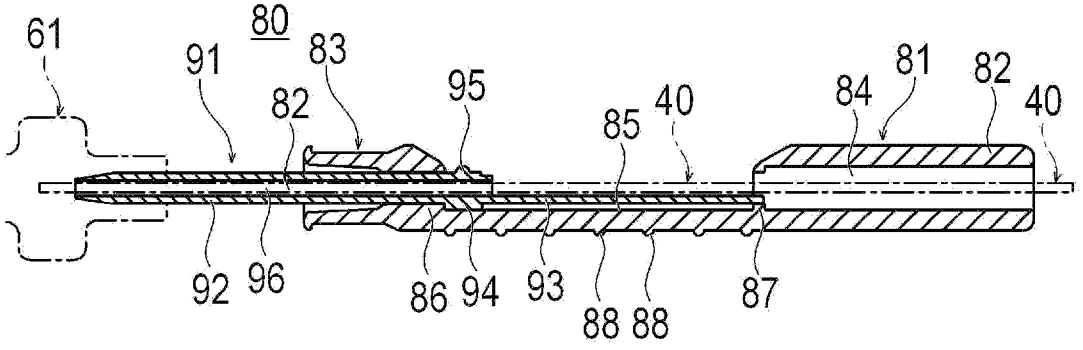
FIG. 7B

INSERTER, MEDICAL ELONGATED BODY SET THAT INCLUDES INSERTER, AND METHOD OF USING INSERTER

This application is a continuation of International Application No. PCT/JP2020/003455 filed on Jan. 30, 2020, which claims priority to Japanese Patent Application No. 2019-026188 filed on Feb. 18, 2019, the entire content of both of which is incorporated herein by reference.

FIELD OF THE INVENTION

The present invention generally relates to an inserter that assists insertion of a medical elongated body into a medical device, a medical elongated body set that accommodates a medical elongated body, and a method of using an inserter.

BACKGROUND DISCUSSION

Electric current flows to a myocardial tissue called an impulse conducting system so that a heart circulates blood by repeatedly contracting and expanding at proper timings. When an electrical signal flowing through the impulse conducting system is abnormally generated or transmitted, the heart cannot contract and expand at proper timings, thereby resulting in arrhythmia.

As a treatment method for arrhythmia, a method is known in which a signal conduction path that causes the arrhythmia is ablated and blocked through heating or cooling. As a device for performing the treatment method, a device is known which can be percutaneously inserted into a left atrium to ablate the signal conduction path located in a pulmonary vein opening. The ablation device configured in this way is widely used since the ablation device is minimally invasive and achieves highly advantageous effects.

When the ablation is performed in the left atrium, a medical procedure called atrial septal puncture (Brockenbrough method) is required. In the medical procedure, a needle punctures a thin partition wall called a fossa ovalis of an atrial septum from a right atrium to open a hole leading to the left atrium from the right atrium. A device for performing the atrial septal puncture is called a transseptal needle. The transseptal needle including a mechanical needle is mainly used owing to low cost. However, when the mechanical needle is used, there is a risk of erroneous puncture since the needle is excessively pressed. When the erroneous puncture of the needle occurs, there is a possibility that the erroneous puncture may cause a serious complication of cardiac tamponade (condition in which a heart failure appears due to the blood accumulated between a pericardium and a myocardium).

As one of the mechanical needles, a guide wire type is known. In the mechanical needle of the guide wire type, a puncture needle is disposed in a distal portion of a flexible guide wire. When the mechanical needle of the guidewire type comes into contact with a wall of the left atrium after opening a hole in the atrial septum and reaching the left atrium, the mechanical needle is bent like the flexible guidewire. In this manner, the erroneous puncture is prevented when the puncture needle is used.

In general, a medical device inserted into a living body requires work (priming) of internally or externally filling the medical device with a physiological salt solution. For example, U.S. Pat. No. 6,059,484 discloses an accommodation tool in which an assisting tool for assisting a guide wire to be inserted into a catheter is provided on a distal side of a tube for holding the guide wire. The accommodation tool can perform the priming on a proximal portion of the guide wire.

SUMMARY

The accommodation tool disclosed in U.S. Pat. No. 6,059,484 can perform the priming on the proximal portion of the guide wire (medical elongated body), but cannot perform the priming on a distal portion. Therefore, when the distal portion of the guide wire removed from the accommodation tool is inserted into the living body, air remaining in the distal portion of the guide wire may cause a possibility of a complication such as an air embolism.

The inserter, medical elongated body set, and method of using an inserter disclosed here can effectively remove air remaining inside a distal portion of a medical elongated body by effectively performing priming on the distal portion of the medical elongated body.

One aspect involves an inserter that assists a medical elongated body to be inserted into a medical device. The inserter includes a tubular portion having a proximal opening portion into which the medical elongated body is inserted, a distal opening portion that guides the medical elongated body to the medical device, and a main lumen through which the proximal opening portion and the distal opening portion communicate with each other, and a connector that communicates with the main lumen of the tubular portion, and connects a liquid injection tool.

According to another aspect, a medical elongated body set includes a medical elongated body in which a needle portion and a cover portion that covers the needle portion to be exposed are disposed in a distal portion of an elongated shaft portion, a holder which is a tubular body that accommodates at least a portion of the medical elongated body, and an inserter connected to an end portion of the holder. The inserter has a tubular portion having a proximal opening portion into which a distal portion of the medical elongated body is inserted, a distal opening portion that guides the medical elongated body to the medical device, and a main lumen through which the proximal opening portion and the distal opening portion communicate with each other, and a connector that communicates with the main lumen of the tubular portion, and connects a liquid injection tool.

A further aspect involves a method of using an inserter. The method includes connecting a liquid injection tool to an inserter connected to an end portion of a holder which is a tubular body that accommodates at least a portion of a medical elongated body, supplying a liquid to the inserter from the liquid injection tool, and performing priming on the medical elongated body, inserting the inserter into the medical device, and inserting the medical elongated body into the medical device from the inserter.

According to the inserter, the medical elongated body set, and the method of using the inserter which are configured as described above, a liquid is injected from a liquid injection tool connected to a connector. In this manner, priming can be performed from a distal portion on a medical elongated body located inside a tubular portion. Therefore, air remaining in the distal portion of the medical elongated body can be effectively removed by effectively performing the priming on the distal portion of the medical elongated body.

BRIEF DESCRIPTION OF THE DRAWINGS

FIGS. 3A and 3B are views illustrating the inserter according to the first embodiment, wherein FIG. 3A is a plan view, and FIG. 3B is a cross-sectional view.

FIGS. 4A-4D are cross-sectional views illustrating a method of using the inserter according to the first embodiment, wherein FIG. 4A illustrates a state where a connector is connected to a liquid injection tool, FIG. 4B illustrates a state where a distal portion of the medical elongated body is accommodated in the inserter, FIG. 4C illustrates a state where the connector is connected to a tubular portion, and FIG. 4D illustrates a state where the medical elongated body is inserted into a medical device by the inserter.

FIGS. 6A and 6B are plan views illustrating an inserter according to a second embodiment, wherein FIG. 6A illustrates a first example, and FIG. 6B illustrates a modification example.

FIGS. 7A and 7B are cross-sectional views illustrating an inserter according to a third embodiment, wherein FIG. 7A illustrates a state where a moving tube is located inside an outer tubular portion, and FIG. 7B illustrates a state where the moving tube protrudes to a distal side from the outer tubular portion.

DETAILED DESCRIPTION

Figure 1:
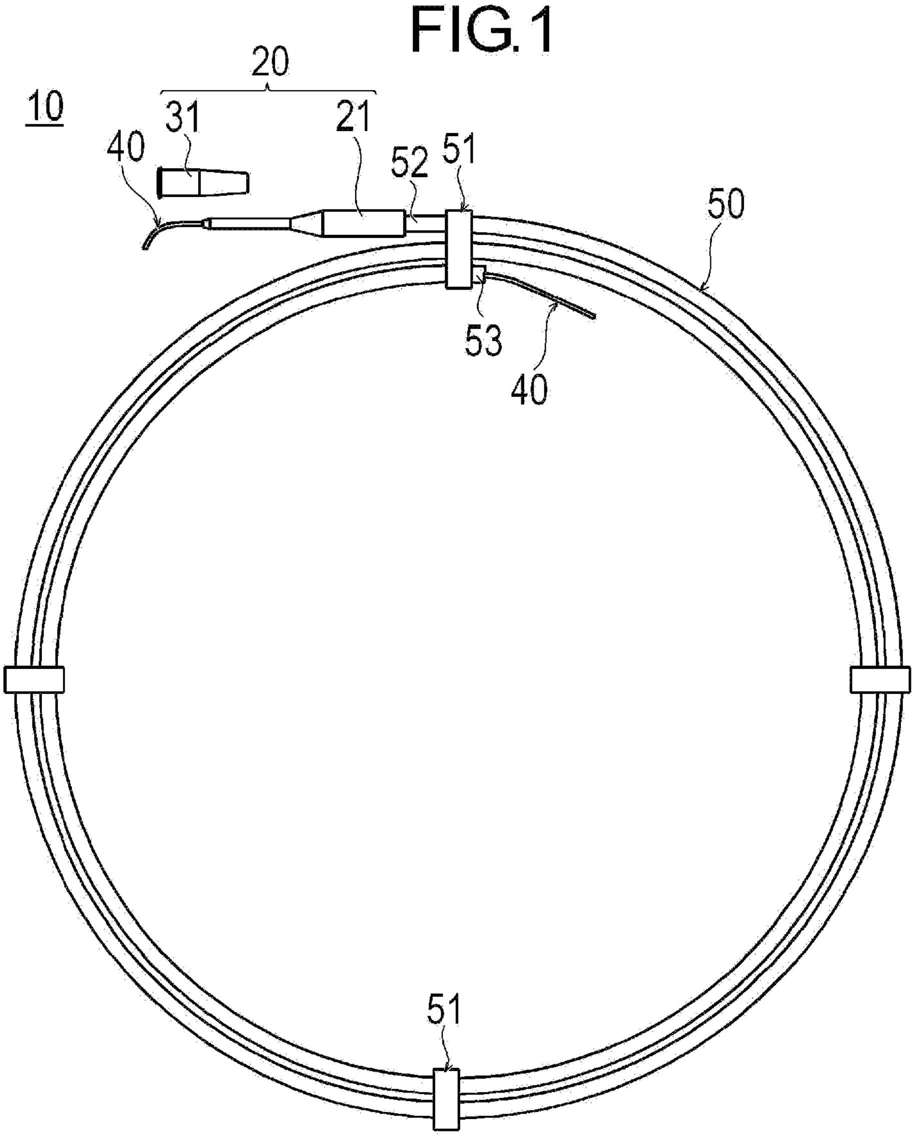
FIG. 1 is a plan view illustrating a medical elongated body set including an inserter according to a first embodiment.

Set forth below with reference to the accompanying drawings is a detailed description of embodiments of an inserter, a medical elongated body set and a method of using an inserter representing examples of the inventive inserter, medical elongated body set and method disclosed here. In some cases, dimensions in the drawings may be exaggerated and differ from actual dimensions for convenience of description. In addition, in the present specification and the drawings, the same reference numerals will be assigned to features or configuration elements having substantially the same function, and so a detailed description of such features/elements, after being once set forth, will not be repeated. In the present specification, a side to be inserted into a lumen will be referred to as a "distal side", and an operating hand-side will be referred to as a "proximal side".

First Embodiment

As illustrated in FIG. 1, an inserter 20 according to a first embodiment is a device included in a medical elongated body set 10 that accommodates a medical elongated body 40 which is a guide wire in order to store and transport the medical elongated body 40. The inserter 20 assists a distal portion of the medical elongated body 40 to be inserted into a medical device 61 (to be described later, refer to FIG. 4D).

The medical elongated body set 10 has a holder 50 which is a pipe body or tubular body for accommodating at least a portion of the medical elongated body 40, a holding portion 51 for holding the holder 50, an inserter 20 connected to an end portion of the holder 50, and the medical elongated body 40 held by the holder 50 and the inserter 20.

A tube extending with a predetermined length is wound around the holder 50, and the holder 50 has a spiral shape as a whole. A shape of the holder 50 is not particularly limited, and may be an elliptical shape, for example. A length of the holder 50 in a major axis direction is shorter than a length of the medical elongated body 40. The inserter 20 is connected to one first end portion 52 of the holder 50. A proximal portion of the medical elongated body 40 is pulled out from a second end portion 53 of the holder 50 to which the inserter 20 is not connected. Therefore, an operator can grip the proximal portion of the medical elongated body 40 pulled out from the second end portion 53 of the holder 50, and can push the proximal portion toward a distal side, can pull the proximal portion toward a proximal side, or can rotate the proximal portion.

The holding portion 51 is a member that holds the spiral shape of the holder 50. In the illustrated embodiment, there are several holding portions 51. The holding portions 51 are disposed at several locations in a winding direction of the holder 50, and fix adjacent tubes to each other in an aligned state.

Figure 2:
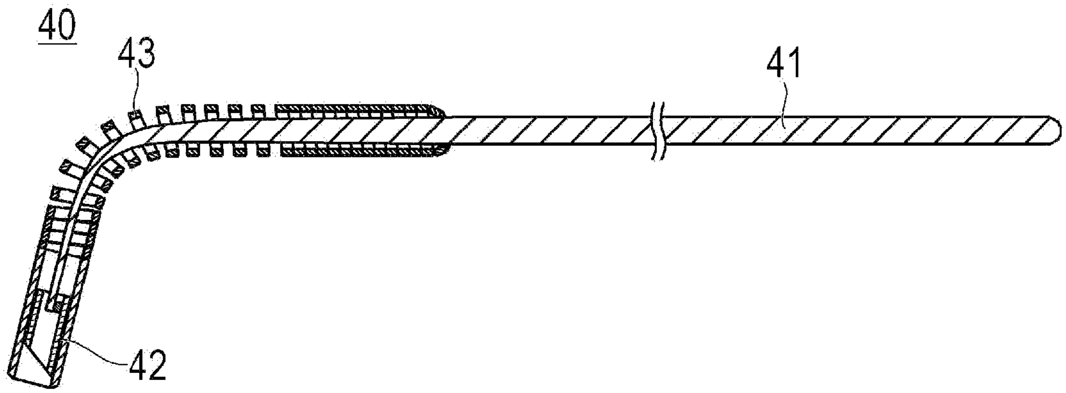
FIG. 2 is a cross-sectional view illustrating a medical elongated body.

As illustrated in FIG. 2, the medical elongated body 40 is a guide wire having a puncturing function. The medical elongated body 40 is used to puncture a fossa ovalis of an atrial septum from a right atrium to form a hole leading from the right atrium to a left atrium. Furthermore, the medical elongated body 40 guides a movement of a dilator (not illustrated) from the right atrium to the left atrium.

The medical elongated body 40 includes a shaft portion (shaft) 41 which is an elongated wire rod, a needle portion (needle) 42 having a sharp needle tip, and a cover portion (cover) 43 that accommodates the needle portion 42. For example, the cover portion 43 may be in the form of a spiral wire rod. Therefore, although the cover portion 43 accommodates the needle portion 42, the cover portion 43 can expose the needle tip of the needle portion 42 by contracting the spiral to reduce pitches of the spiral.

In general, the guide wire has a certain degree of rigidity and high flexibility so that the guide wire does not damage an insertion target body lumen and can be pushed forward into a meandering body lumen. Therefore, when the medical elongated body 40, which is the guide wire, receives a force acting toward the proximal side in the distal end of the cover portion 43 in a state where bending (deformation in a radial direction) is not restricted, any site of the medical elongated body 40 is bent, and the force escapes to the other site from the distal end of the cover portion 43. Therefore, even when the cover portion 43 receives the force acting toward the proximal side in the distal end, the force required for contracting the cover portion 43 does not act on the cover portion 43. Therefore, the cover portion 43 is bent by receiving the force acting toward the proximal side in a freely bendable state, and maintains a state where the needle portion 42 is accommodated. When the medical elongated body 40 is inserted into a tubular body such as a medical device 61 and a dilator (to be described later), the bending is restricted. In this state, the distal end of the medical elongated body 40 abuts against or contacts the fossa ovalis so that the cover portion 43 contracts and the needle portion 42 protrudes. In this manner, the medical elongated body 40 can form a hole in the fossa ovalis.

Figure 3A:
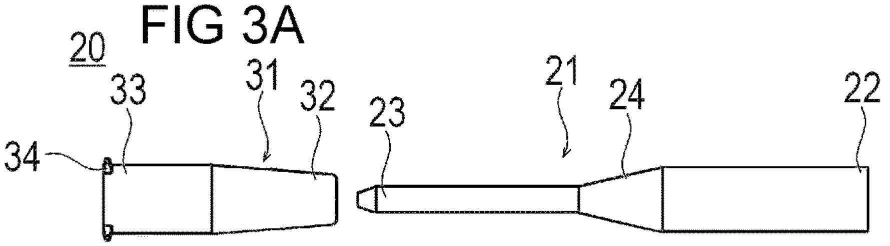
Figure 3B:
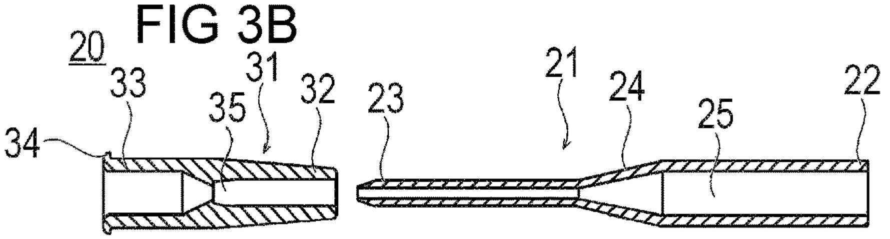

As illustrated in FIGS. 1 and 3, the inserter 20 has a tubular portion 21 (tubular body) connected to the holder 50 and a connector 31 connectable to the tubular portion 21.

The tubular portion 21 has a proximal opening portion 22 connected to the holder 50, a distal opening portion 23 that can be connected to the connector 31, and a decreased diameter portion 24 located between the proximal opening portion 22 and the distal opening portion 23. The proximal opening portion 22 covers an end portion of the holder 50, and is connected to the holder 50. The proximal opening portion 22 can be detached from the holder 50. The tubular portion 21 internally has a main lumen 25 penetrating the distal opening portion 23 from the proximal opening portion 22. Depending on an outer diameter of the holder 50 and an inner diameter of the connector 31, an inner diameter of the decreased diameter portion 24 may be the same as an inner diameter of the tubular portion 21. In addition, the proximal opening portion 22 may be separated from the end portion of the holder 50.

The distal opening portion 23 can be connected to the connector 31, and can be inserted into the medical device 61 in order to guide the medical elongated body 40 to the medical device 61. The outer diameter and the inner diameter of the distal opening portion 23 are smaller than the outer diameter and the inner diameter of the proximal opening portion 22. Furthermore, the outer diameter and the inner diameter of the distal opening portion 23 are smaller than the inner diameter of the medical device 61. Therefore, the distal opening portion 23 can easily guide the medical elongated body 40 to the thin medical device 61. The outer diameter of the distal end of the distal opening portion 23 decreases toward the distal side in a tapered shape. In this manner, the distal opening portion 23 is likely to be inserted into the connector 31 or the medical device 61. The medical device 61 is a reinforcement tube inserted into a dilator to widen a hole formed by the medical elongated body 40 in the fossa ovalis in an atrial septal puncture, for example. The medical device 61 may be the dilator.

The decreased diameter portion 24 is a portion where the inner diameter and the outer diameter are changed between the larger proximal opening portion 22 that can cover the holder 50 and the smaller distal opening portion 23 that can be inserted into the medical device 61. The inner diameter and the outer diameter of the decreased diameter portion 24 decrease toward the distal side in a tapered shape. A tapered inner surface of the decreased diameter portion 24 serves to smoothly guide the medical elongated body 40 located therein to the distal side.

The connector 31 has an interlock portion 32 that can be interlocked with the distal opening portion 23 of the tubular portion 21 and an injection tool interlock portion 33 that can be connected to a liquid injection tool 60 (refer to FIG. 4). The distal opening portion 23 can be connected to an inner surface of the interlock portion 32. For example, the connection means combination or contact. Therefore, the inner diameter of the interlock portion 32 substantially coincides with the outer diameter of the distal opening portion 23. For example, a distal tube of the liquid injection tool 60 which is a syringe can be fitted to an inner surface of the injection tool interlock portion 33. Therefore, the inner diameter of the injection tool interlock portion 33 substantially coincides with the outer diameter of the distal tube of the liquid injection tool 60. An outer surface of the injection tool interlock portion 33 has a projection portion 34 that can be connected to a rotary connector (not illustrated) rotatably provided on the distal tube or distal portion of the liquid injection tool 60. The projection portion 34 may not be provided. The connector 31 has a connector lumen 35 penetrating the interlock portion 32 from the injection tool interlock portion 33.

The inner diameter of the distal opening portion 23 is not particularly limited, but is 0.1 to 10 mm, for example. The outer diameter of the distal opening portion 23 is not particularly limited, but is 0.2 to 20 mm, for example. The inner diameter of the proximal opening portion 22 is not particularly limited, but is 0.5 to 25 mm, for example. The outer diameter of the proximal opening portion 22 is not particularly limited, but is 1 to 50 mm, for example. The inner diameter of the injection tool interlock portion 33 is not particularly limited, but is 0.4 to 40 mm, for example.

The material used to fabricate the tubular portion 21 and the connector 31 is not particularly limited as long as the materials have a certain level of strength. For example, polyolefin such as polyethylene, polypropylene, and ethylene-propylene copolymer, or various resin materials such as polyvinyl chloride, polystyrene, polyamide, and polycarbonate, and acrylic resins can be adopted. The material used to fabricate the tubular portion 21 and the connector 31 may be a metallic material.

Figure 5:
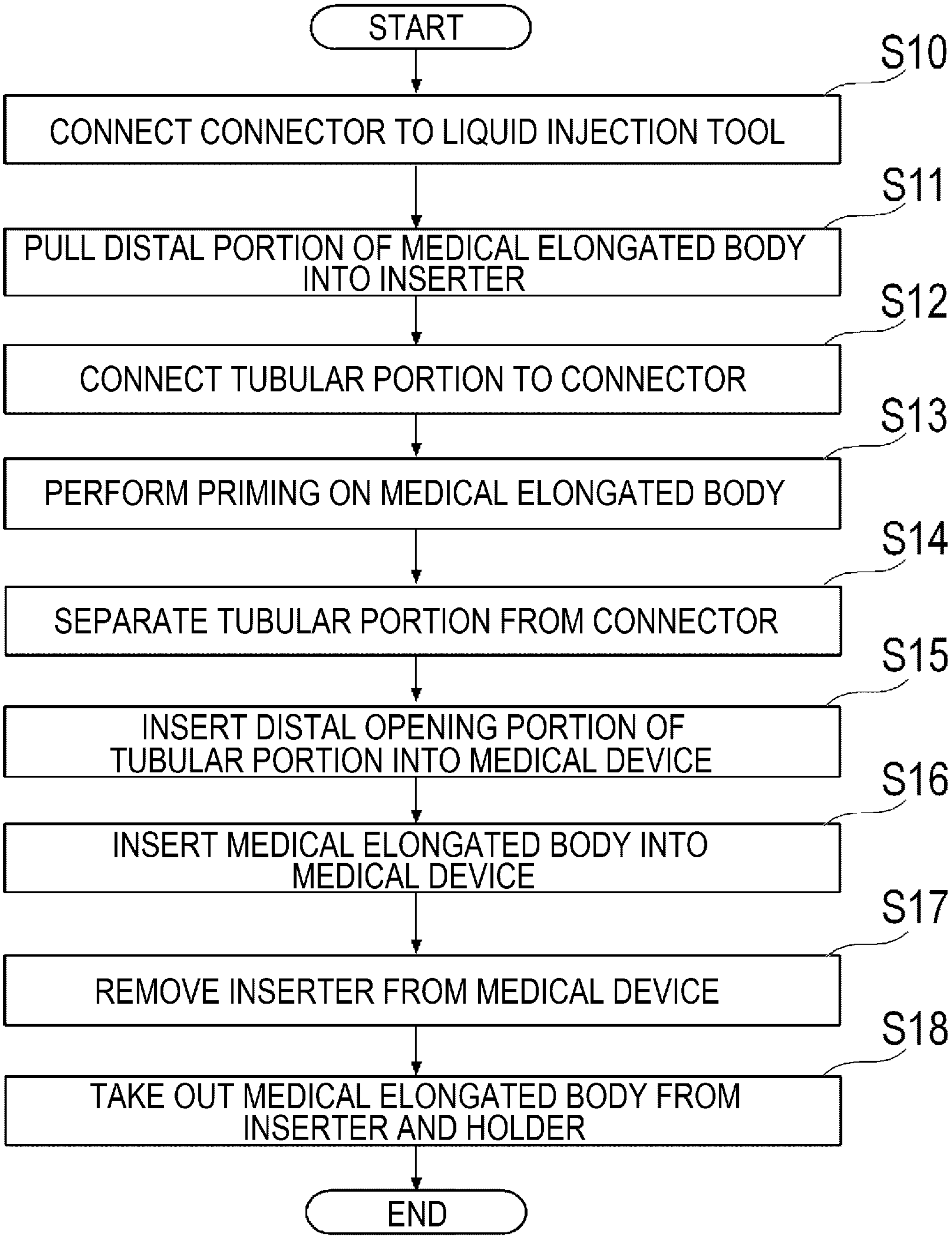
FIG. 5 is a flowchart illustrating a method of using the inserter according to the first embodiment.

Next, a method of using the inserter 20 according to the first embodiment will be described with reference to a flowchart illustrated in FIG. 5.

Figure 4A:
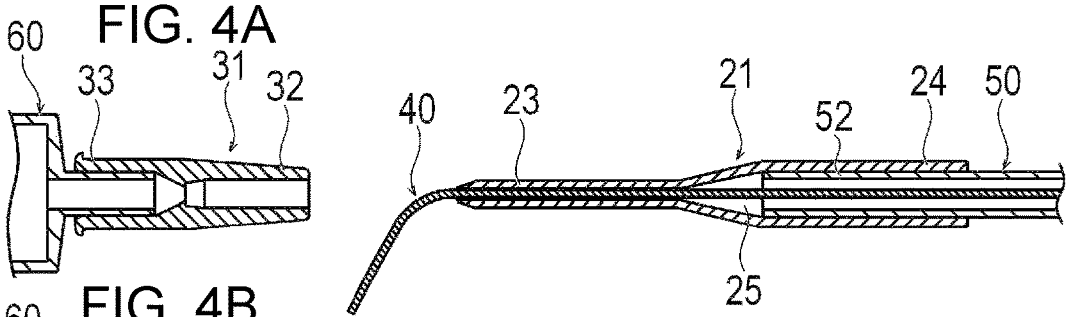

First, as illustrated in FIG. 4A, an operator inserts the distal tube (distal portion) of the liquid injection tool 60 into the injection tool interlock portion 33 of the connector 31. In this manner, the connector 31 is connected to the liquid injection tool 60 (Step S10). The distal portion of the medical elongated body 40 is in a state where the distal portion is pulled out to the distal side from the distal opening portion 23 of the inserter 20. That is, the distal portion of the medical elongated body 40 is positioned distally beyond the distal opening portion 23 of the inserter 20 as shown in FIG. 4A.

Figure 4B:
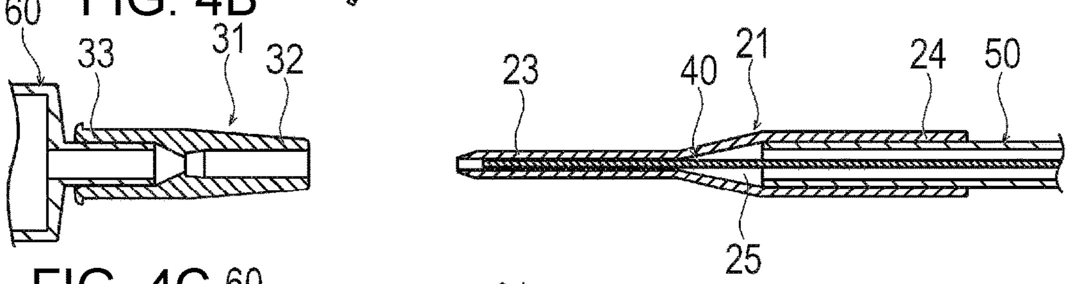

Next, as illustrated in FIG. 4B, the operator pulls the proximal portion of the medical elongated body 40 pulled out from a second end portion 53 on a side opposite to a side to which the inserter 20 of the holder 50 is connected. In this manner, the distal portion of the medical elongated body 40 is pulled into the main lumen 25 inside the inserter 20 (inside the tubular portion 31 of the inserter 20) (Step S11). In this manner, the inserter 20 is in a state where the distal opening portion 23 of the tubular portion 21 can be connected to the interlock portion 32 of the connector 31.

Figure 4C:
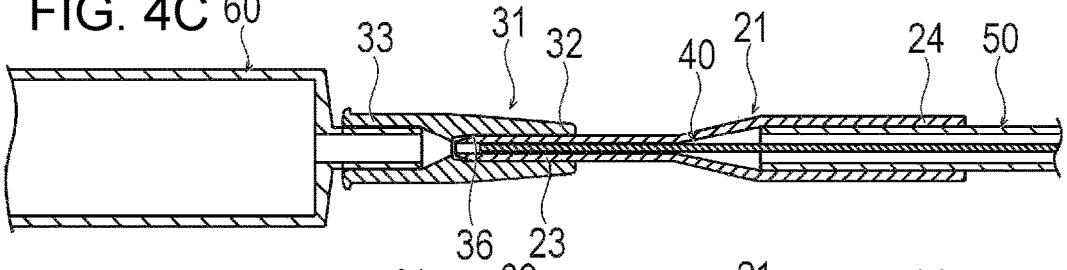

Next, as illustrated in FIG. 4C, the operator connects the distal opening portion 23 of the tubular portion 21 to the interlock portion 32 of the connector 31 (Step S12). A distal surface or an outer peripheral surface located in the distal portion of the distal opening portion 23 is attached to a first attachment portion 36 located on an inner peripheral surface of the interlock portion 32. Next, the operator releases a liquid such as a physiological salt solution from the liquid injection tool 60. In this manner, the liquid is injected into the main lumen 25 of the tubular portion 21 through the connector 31. The liquid injected into the main lumen 25 fills the inside of the inserter 20, and further flows into the holder 50. The liquid flowing into the holder 50 fills the inside of the holder 50, and is removed from a second end portion 53 of the holder 50. In this manner, priming can be performed from the distal side on the medical elongated body 40 inside the inserter 20 and the holder 50 (Step S13).

Figure 4D:
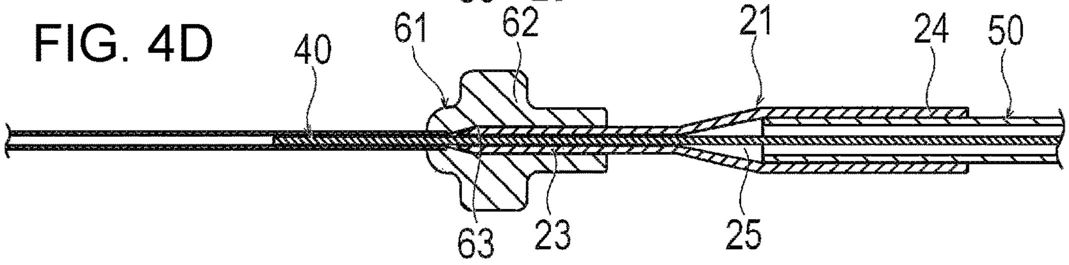

Next, the operator separates the distal opening portion 23 of the tubular portion 21 from the interlock portion 32 of the connector 31 (Step S14). Next, as illustrated in FIG. 4D, the operator inserts the distal opening portion 23 of the tubular portion 21 into an opening portion on the proximal side of the medical device 61 (Step S15). A distal surface or an outer peripheral surface located in the distal portion of the distal opening portion 23 is attached to a second attachment portion 63 located on an inner peripheral surface of a hub 62 of the medical device 61. The hub 62 is a portion that enables other devices to be inserted or to be connected. Next, the operator pushes the medical elongated body 40 pulled out from the second end portion 53 of the holder 50, and inserts the medical elongated body 40 into the medical device 61 (Step S16). Next, in a state where the medical elongated body 40 is left inside the medical device 61, the distal opening portion 23 of the tubular portion 21 is removed from the medical device 61 (Step S17). The holder 50 may be detached from the proximal opening portion 22 of the tubular portion 21, before the distal opening portion 23 of the tubular portion 21 is removed from the medical device 61. Next, the whole medical elongated body 40 is taken out to the distal side from the holder 50 and the inserter 20 (Step S18). Thereafter, the operator can perform a medical procedure using the medical device 61.

As described above, the inserter 20 according to the first embodiment is the inserter 20 that assists the medical elongated body 40 to be inserted into the medical device 61, and the inserter 20 includes the tubular portion 21 having the proximal opening portion 22 into which the medical elongated body 40 is inserted and the distal opening portion 23 that guides the medical elongated body 40 to the medical device 61, and having the main lumen 25 through which the proximal opening portion 22 and the distal opening portion 23 communicate with each other, and the connector 31 that can communicate with the main lumen 25 of the tubular portion 21 and can connect the liquid injection tool 60.

The inserter 20 configured as described above injects the liquid from the liquid injection tool 60 connected to the connector 31. In this manner, priming can be performed from the distal portion on the medical elongated body 40 located in the main lumen 25 of the tubular portion 21. Therefore, the inserter 20 can effectively remove air remaining inside the distal portion by effectively performing the priming on the distal portion of the medical elongated body 40.

In addition, the connector 31 can be connected to the distal opening portion 23 of the tubular portion 21. In this manner, the inserter 20 injects the liquid from the connector 31 connected to the distal opening portion 23 so that the priming can be effectively performed from the distal side on the medical elongated body 40 located in the main lumen 25 of the tubular portion 21.

In addition, the medical elongated body set 10 in the present embodiment has the medical elongated body 40 in which the needle portion 42 and the cover portion 43 that covers the needle portion 42 to be exposed are disposed in the distal portion of the elongated shaft portion 41, the holder 50 which is a tubular body that accommodates at least a portion of the medical elongated body 40, and the inserter 20 connected to an end portion of the holder 50. The inserter 20 has the tubular portion 21 having the proximal opening portion 22 into which the distal portion of the medical elongated body 40 is inserted and the distal opening portion 23 that guides the medical elongated body 40 to the medical device 61, and having the main lumen 25 through which the proximal opening portion 22 and the distal opening portion 23 communicate with each other, and the connector 31 that communicates with the main lumen 25 of the tubular portion 21, and connects the liquid injection tool 60.

The medical elongated body set 10 configured as described above injects the liquid from the liquid injection tool 60 connected to the connector 31 of the inserter 20 so that the priming can be performed from the distal portion on the medical elongated body 40 located in the main lumen 25 of the tubular portion 21. Therefore, the medical elongated body set 10 can effectively remove the air remaining inside the cover portion 43 located in the distal portion of the medical elongated body 40.

In addition, the medical elongated body set 10 has the dilator or the reinforcement tube that can be inserted into the dilator as the medical device 61. The connector 31 has the interlock portion 32 which the distal opening portion 23 can be inserted into and connected to. The inner diameter of the lumen of the hub 62 of the medical device 61 is substantially coincides with the inner diameter of the interlock portion 32. In this manner, the distal opening portion 23 of the tubular portion 21 can be satisfactorily connected to the interlock portion 32 of the connector 31, and can be satisfactorily connected to the hub 62 of the medical device 61.

In addition, the distal portion of the distal opening portion 23 can be attached to the first attachment portion 36 of the connector 31 and the second attachment portion 63 of the hub 62 of the medical device 61. In this manner, the distal portion of the distal opening portion 23 can be satisfactorily connected to the hub 62 and the interlock portion 32 of the medical device 61.

In addition, the method of using the inserter 20 in the present embodiment includes Step S10 of connecting the liquid injection tool 60 to the inserter 20 connected to the end portion of the holder 50 which is the tubular body that accommodates at least a portion of a medical elongated body 40, Step S13 of supplying the liquid to the inserter 20 from the liquid injection tool 60, and performing priming on the medical elongated body 40, Step S15 of inserting the inserter 20 into the medical device 61, and Step S16 of inserting the medical elongated body 40 into the medical device 61 from the inserter 20.

According to the method of using the inserter 20 configured as described above, the liquid is injected from the liquid injection tool 60 connected to the inserter 20 so that the priming can be performed from the distal portion on the medical elongated body 40 disposed inside the inserter 20. Therefore, the inserter 20 can effectively remove the air remaining inside the distal portion of the medical elongated body 40. Then, the medical elongated body 40 on which the priming is satisfactorily performed can be easily inserted into the medical device 61 via the inserter 20 by an operator.

In addition, the above-described method of using the inserter 20 has Step S11 of pulling the distal portion of the medical elongated body 40 protruding distally beyond the distal end of the tubular portion 21 of the inserter 20 into the inserter 20, before the step of connecting the liquid injection tool 60 to the inserter 20. In this manner, the liquid can be injected into the inserter 20 in a state where the distal portion of the medical elongated body 40 is disposed inside the inserter 20 (inside the tubular portion 21 of the inserter 20). Therefore, the operator can effectively perform the priming on the distal portion of the medical elongated body 40 disposed inside the medical elongated body 40.

Second Embodiment

An inserter 70 according to a second embodiment is different from that according to the first embodiment in that a connector 71 is integrated with the tubular portion 21 as illustrated in FIG. 6A.

The connector 71 is formed in an auxiliary tube 73 bifurcated from the tubular portion 21. The auxiliary tube 73 has an auxiliary lumen 72 communicating with the main lumen 25. In this manner, in the inserter 70, the liquid is injected from the connector 71 formed in the auxiliary tube 73 so that the priming can be effectively performed from the distal side on the medical elongated body 40 located in the main lumen 25 of the tubular portion 21. Furthermore, the connector 71 is not disposed in the distal opening portion 23.

Accordingly, the movement of the medical elongated body 40 from the proximal opening portion 22 to the distal opening portion 23 is not hindered by the liquid injection tool 60 connected to the connector 71. In addition, the liquid injection tool 60 can be connected to the connector 71 without using a separate connector. Accordingly, the priming can be easily performed.

The connector 71 may be disposed in the auxiliary tube 73 such that the connector 71 is detachable from the auxiliary tube 73. A detachable structure can be similar to a structure (refer to FIG. 3) of the connector 31 with respect to the distal opening portion 23 according to the first embodiment.

As a modification example of the inserter 70 according to the second embodiment, as illustrated in FIG. 6B, the connector 71 may be inserted into the liquid injection tool 60 instead of covering the liquid injection tool 60. In this case, the connector 71 has the outer diameter that can be inserted into the liquid injection tool 60. It is preferable that the outer diameter of the connector 71 is different from the outer diameter of the distal opening portion 23. In this manner, the connector 71 can be connected only to the liquid injection tool 60, and the distal opening portion 23 can be connected only to the medical device 61. Therefore, it is possible to suppress a possibility that the operator may make a mistake in selecting a connecting destination of the liquid injection tool 60 and the medical device 61. The outer diameter of the connector 71 may be the same as the outer diameter of the distal opening portion 23. In this case, the connector 71 and the distal opening portion 23 can be connected to both the liquid injection tool 60 and the medical device 61. Therefore, for example, the liquid injection tool 60 can be connected to the distal opening portion 23, and the priming can be performed from the distal opening portion 23. In this case, the distal opening portion 23 also functions as the connector 71. In a case where the distal opening portion 23 can also function as the connector 71, the auxiliary tube 73 and the auxiliary lumen 72 in FIG. 6B may be omitted.

Third Embodiment

An inserter 80 according to a third embodiment is different from that according to the first embodiment in that a distal opening portion 92 which can be connected to the medical device 61 can protrude from the connector 83 as illustrated in FIGS. 7A and 7B.

The inserter 80 has an outer tubular portion 81, a moving tube 91 disposed to be movable inside the outer tubular portion 81, and a connector 83 integrally formed with the outer tubular portion 81.

The outer tubular portion 81 has a proximal opening portion 82 connected to the holder 50. The proximal opening portion 82 covers the first end portion 52 of the holder 50, and is connected to the holder 50 to be detachable therefrom. The outer tubular portion 81 internally has an outer lumen 84 penetrating the connector 83 from the proximal opening portion 82. The outer tubular portion 81 has a lateral exposure surface (opening) 85 so that an inner surface of the outer tubular portion 81 at the lateral exposure surface 85 is exposed in a direction intersecting with an axis of the outer lumen 84. The lateral exposure surface 85 is also a portion of the outer lumen 84. The moving tube 91 is exposed from the lateral exposure surface (opening) 85. A distal locking portion 86 and a proximal locking portion 87, each having a decreased or reduced inner diameter, are formed on the distal side and the proximal side on which the lateral exposure surface 85 of the outer lumen 84 is pinched therebetween. A convex portion 88 for slip stopping or prevention (grip enhancement) is formed on the outer peripheral surface of the outer tubular portion 81. It is preferable that the convex portion 88 is formed on the outer peripheral surface of the lateral exposure surface 85. In this manner, the operator is likely to operate a portion exposed from the lateral exposure surface 85. The convex portion 88 may be formed in another portion on the outer peripheral surface of the outer tubular portion 81.

The moving tube 91 has a tubular distal opening portion 92 (tubular part) having the moving lumen 96, and an axially projecting support portion 93 located on the proximal side from the distal opening portion 92. The outer peripheral surface of the proximal portion of the distal opening portion 92 has a locking convex portion (locking protrusion) 94 protruding toward the lateral exposure surface 85, and an operating convex portion (operating protrusion) 95 protruding in a direction opposite the locking convex portion. The moving tube 91 moves to the distal side or in the distal direction inside the outer lumen 84 of the outer tubular portion 81. In this manner, the locking convex portion 94 comes into contact with the distal locking portion 86 in a distal-most axial position of the moving tube 91, and further axial movement of the moving tube 91 in the distal direction is restricted. The moving tube 91 moves to the proximal side or in the proximal direction inside the outer lumen 84 of the outer tubular portion 81. In this manner, the locking convex portion 94 comes into contact with the proximal locking portion 87 in a proximal-most position of the moving tube, and further axial movement of the moving tube 91 in the proximal direction is restricted. In this manner, the moving tube 91 is satisfactorily held without falling off from the outer tubular portion 81. The operating convex portion 95 is a portion operated by the operator with a finger, when the moving tube 91 is moved to the distal side or the proximal side with respect to the outer tubular portion 81.

As illustrated in FIG. 7A, the liquid injection tool 60 can be connected to the connector 83 in a state where the moving tube 91 is located inside the outer tubular portion 81. In this case, a length L1 along the axis of the moving lumen 96 formed in the distal opening portion 92 is longer than a length L2 along the axis of the lateral exposure surface 85. Therefore, the liquid injected from the liquid injection tool 60 does not leak from the lateral exposure surface 85, and can flow to the proximal side through the moving lumen 96.

As illustrated in FIG. 7B, the distal opening portion 92 can be inserted into the medical device 61 in a state where the moving tube 91 protrudes to the distal side from (i.e., protrudes distally beyond) the outer tubular portion 81. The moving tube 91 having the distal opening portion 92 and the outer tubular portion 81 having the proximal opening portion 82 form the tubular portion having the main lumen. That is, the main lumen is formed by the moving lumen 96 and the outer lumen 84. The support portion 93 is located on the proximal side from the moving lumen 96, and is disposed on a side where the lateral exposure surface 85 is located with respect to the axis of the outer lumen 84. The medical elongated body 40 passes through the moving lumen 96 to be located away from the lateral exposure surface 85 on the proximal side of the moving lumen 96. The support portion 93 supports the medical elongated body 40 located away from the lateral exposure surface 85.

As described above, the inserter 80 according to the third embodiment has the outer tubular portion 81 integrated with the connector 83 (the outer tubular portion 81 and the connector 83 are a one-piece structure), and having the proximal opening portion 82 and the outer lumen 84 through which the proximal opening portion 82 communicates with the connector 83, and the moving tube 91 disposed to be movable along the axis of the outer lumen 84 inside the outer lumen 84, and internally having the moving lumen 96. The moving tube 91 has the distal opening portion 92 formed on the distal side. The moving lumen 96 communicates with the outer lumen 84. The moving tube 91 can protrude to the distal side from the connector 83. In this manner, the inserter 80 can connect the liquid injection tool 60 to the connector 83 by moving the moving tube 91 to the proximal side. Therefore, the distal opening portion 92 does not interfere with the connection, when the liquid injection tool 60 is connected to the connector 83. Furthermore, the inserter 80 can insert the moving tube 91 into the medical device 61 by moving the moving tube 91 to the distal side and causing the moving tube 91 to protrude to the distal side from the connector 83.

In addition, the outer tubular portion 81 has the lateral exposure surface 85 whose inner surface is exposed in a direction intersecting with the axis of the outer lumen 84. In this manner, in the inserter 80, the medical elongated body 40 can be exposed outward from the lateral exposure surface 85. Therefore, the operator can operate the medical elongated body 40 exposed from the lateral exposure surface 85. Accordingly, for example, the operator can operate the medical elongated body 40 exposed from the lateral exposure surface 85 with fingers of a hand gripping the inserter 80. Therefore, the operator can operate the inserter 80 and the medical elongated body 40 with one hand, and can operate the other device with the other hand. In addition, although the needle portion 42 is disposed in the distal portion of the medical elongated body 40, the operator can safely operate the medical elongated body 40 without touching the needle tip of the needle portion 42. In addition, the operator does not need to touch the distal portion of the medical elongated body 40. Accordingly, it is possible to suppress damage to the distal portion of the medical elongated body 40.

In addition, the outer tubular portion 81 has the lateral exposure surface 85 whose inner surface is exposed in the direction intersecting with the axis of the outer lumen 84, and the length in the direction along the axis of the moving lumen 96 is longer than the length in the direction along the axis of the lateral exposure surface 85. In other words, the axial length of the moving lumen 96 is greater than the axial length of the lateral exposure surface 85. In this manner, the moving tube 91 accommodated in the outer tubular portion 81 can close the lateral exposure surface 85. Therefore, it is possible to suppress a possibility that a priming liquid injected from the connector 83 may leak out.

In addition, the outer tubular portion 81 has the lateral exposure surface 85 whose inner surface is exposed in the direction intersecting with the axis of the outer lumen 84. The moving tube 91 has the support portion 93 disposed on the proximal side from the moving lumen 96, and disposed on a side where the lateral exposure surface 85 is located with respect to the axis of the outer lumen 84. In a state where the moving tube 91 protrudes to the distal side from the outer tubular portion 81, the support portion 93 is exposed on the lateral exposure surface 85. In a state where the moving tube 91 is located inside the outer tubular portion 81, a portion from the distal end to the proximal end of the support portion 93 is located inside the outer tubular portion 81. In this manner, in the inserter 80, the medical elongated body 40 can be exposed outward while being supported by the support portion 93 on the lateral exposure surface 85 exposed outward. Therefore, the operator can satisfactorily operate the medical elongated body 40 exposed outward. In this case, the medical elongated body 40 located away from the lateral exposure surface 85 passes through the moving lumen 96 to be supported by the support portion 93 located on the proximal side of the moving lumen 96. Therefore, the operator is likely to transmit a force to the medical elongated body 40. In addition, the operator can operate the medical elongated body 40 exposed from the lateral exposure surface 85 with the fingers of the hand gripping the inserter 80. Therefore, the operator can operate the inserter 80 with one hand, and can operate the other device with the other hand. In addition, when the needle portion 42 is located in the distal end of the medical elongated body 40, the operator can safely operate the medical elongated body 40 without touching the needle tip of the needle portion 42. In addition, the operator does not need to touch the distal portion of the medical elongated body 40. Accordingly, it is possible to suppress damage to the distal portion of the medical elongated body 40.

Fourth Embodiment

Figure 8:
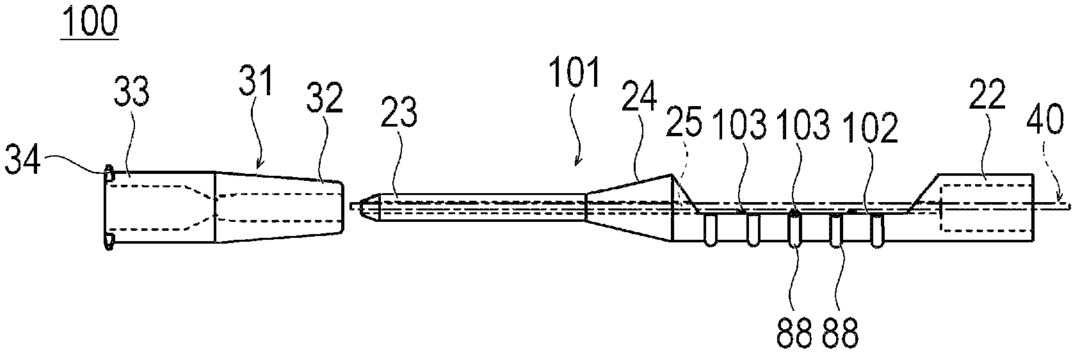
FIG. 8 is a plan view illustrating an inserter according to a fourth embodiment.

An inserter 100 according to a fourth embodiment is different from that according to the first embodiment in that a lateral exposure surface 102 is formed in a tubular portion 101 as illustrated in FIG. 8.

The tubular portion 101 has the lateral exposure surface 102 whose inner surface is exposed in the direction intersecting with the axis of the main lumen 25. Therefore, the operator can satisfactorily operate the medical elongated body 40 exposed outward from the lateral exposure surface 102. The operator can operate the medical elongated body 40 exposed from the lateral exposure surface 102 with the fingers of the hand gripping the inserter 100. The lateral exposure surface 102 has at least one supporting convex portion (at least one supporting projection) 103. The supporting convex portion 103 serves to cause the medical elongated body 40 to float from the lateral exposure surface 102. In this manner, the operator is likely to touch the medical elongated body 40, and easily operates the medical elongated body 40.

Fifth Embodiment

Figure 9:
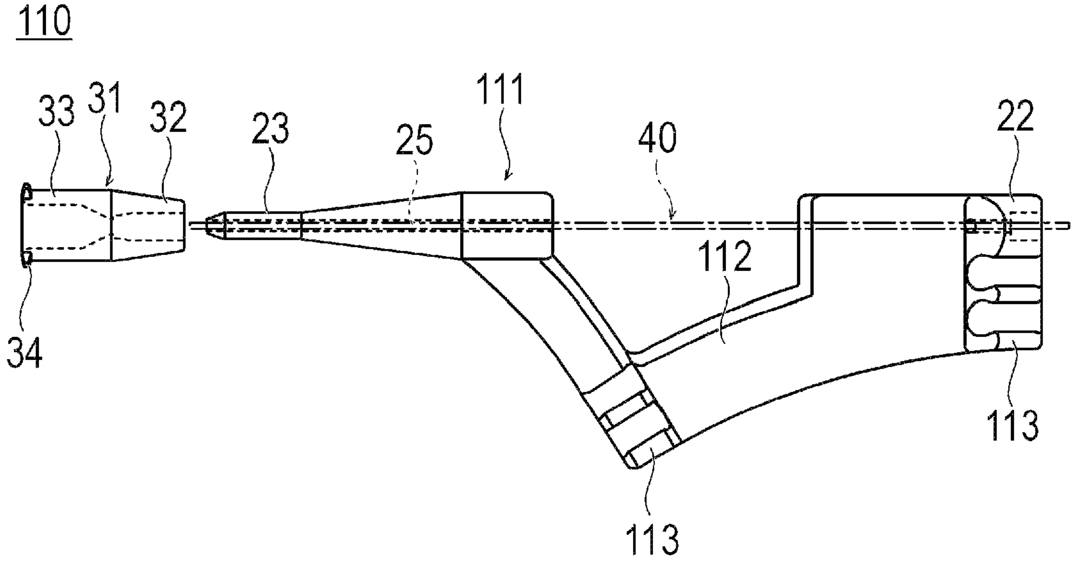
FIG. 9 is a plan view illustrating an inserter according to a fifth embodiment.

An inserter 110 according to a fifth embodiment is different from that according to the first embodiment in that a support body 112 is provided between the proximal opening portion 22 and the distal opening portion 23 of a tubular portion 111 as illustrated in FIG. 9.

The tubular portion 111 has the support body 112 having a holding portion 113 for holding the holder 50 to be wound. That is, the holding portion 113 of the support body 112 id configured to hold the holder 50 while the holder 50 is in a wound state. The support body 112 extends to be curved in a direction away from the main lumen 25 from each of the proximal opening portion 22 and the distal opening portion 23. Therefore, a space is formed between the proximal opening portion 22 and the distal opening portion 23. Therefore, the operator can easily operate the medical elongated body 40 located in this space.

The present invention is not limited only to the above-described embodiments, and various modifications can be made by those skilled in the art within the technical idea of the present invention. For example, the medical elongated body 40 is not particularly limited as long as the medical elongated body 40 is an elongated device inserted into a living body. For example, the medical elongated body may be a device such as a guide wire or a catheter having no needle portion.

In addition, in the inserter 80 according to the third embodiment, the lateral exposure surface 85 may not be formed, and the moving tube 91 may not be exposed in an intermediate portion of the outer tubular portion 81. A spring that biases the moving tube 91 in a distal direction may be disposed inside the outer tubular portion 81.

In addition, a structure similar to the supporting convex portion 103 formed on the lateral exposure surface 102 of the inserter 100 according to the fourth embodiment may be formed in the support portion 93 of the inserter 80 according to the third embodiment.

In addition, the structure in each of the above-described embodiments can be appropriately applied to other embodiments.

The detailed description above describes embodiments of an inserter, a medical elongated body set that includes an inserter, and a method of using an inserter representing examples of the inventive inserter, medical elongated body set and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of using an inserter, comprising:

connecting a liquid injection tool to a tubular portion of the inserter that is connected to an end portion of a tubular holder in which is accommodated at least a portion of a medical elongated body;

supplying a liquid to the inserter from the liquid injection tool to perform priming on the medical elongated body;

inserting the tubular portion of the inserter into a medical device, the supplying of the liquid to the inserter occurring before the inserting of the tubular portion of the inserter into the medical device; and inserting the medical elongated body into the medical device from the inserter.

2. The method of using an inserter according to claim 1, wherein before the connecting of the liquid injection tool to the tubular portion of the inserter, a distal portion of the medical elongated body is located distal of a distal end of the tubular portion of the inserter, the method further comprising: pulling the distal portion of the medical elongated body in a proximal direction to position the distal portion of the medical elongated body proximal of the distal end of the tubular portion of the inserter, the pulling of the distal portion of the medical elongated body in the proximal direction occurring before the connecting of the liquid injection tool to the tubular portion of the inserter.

3. The method of using an inserter according to claim 1, wherein the inserter comprises a tubular portion and a connector, the method further comprising moving the connector towards the tubular portion and connecting the connector to the tubular portion before the supplying of the liquid to the inserter from the liquid injection tool, the connecting of the connector to the tubular portion occurring when the tubular portion is connected to the end portion of the tubular holder.

4. The method of using an inserter according to claim 1, wherein the connecting of the liquid injection tool to the tubular portion of the inserter occurs before the supplying of the liquid to the inserter from the liquid injection tool.

5. The method of using an inserter according to claim 1, wherein the inserter comprises a connector that is connected to the tubular portion of the inserter during the supplying of the liquid to the inserter from the liquid injection tool and that is disconnected from the tubular portion of the inserter during the inserting of the tubular portion of the inserter into the medical device.

6. The method of using an inserter according to claim 1, wherein the inserter comprises a connector, the connector having a connector lumen extending through the connector, the tubular portion having a main lumen extending through the tubular portion, the connecting of the liquid injection tool to the tubular portion of the inserter comprising connecting one end of the connector and one end of the tubular portion to one another so that that the connector lumen and the main lumen are in fluid communication with one another.

7. The method of using an inserter according to claim 6, further comprising, after the supplying of the liquid to the inserter, separating the one end of the connector and the one end of the tubular portion from one another, and the inserting of the tubular portion of the inserter into the medical device comprising inserting the one end of the tubular portion into the medical device.

8. The method of using an inserter according to claim 1, wherein the inserter comprises a connector, the tubular portion of the inserter having one end and an opposite end, the inserting of the tubular portion of the inserter into the medical device comprising inserting the one end of the tubular portion into the medical device while the tubular holder is connected to the opposite end of the tubular portion.

9. The method of using an inserter according to claim 8, wherein the inserting of the medical elongated body into the medical device comprises advancing the medical elongated body in a forward direction through an opening at the one end of the tubular portion.

10. A method of using an inserter, comprising:

connecting a liquid injection tool to a tubular portion of the inserter that is connected to a first end portion of a tubular holder in which is accommodated at least a portion of a medical elongated body, the tubular holder also having a second end portion opposite the first end portion;

supplying a liquid to the inserter from the liquid injection tool so that the liquid fills an inside of the inserter, flows into the tubular holder, fills an inside of the tubular holder and is discharged by way of the second end portion of the tubular holder to perform priming on the medical elongated body;

inserting the tubular portion of the inserter into a medical device; and advancing the medical elongated body relative to the tubular portion of the inserter and relative to the medical device to move at least a portion of the medical elongated body into the medical device while the tubular portion of the inserter is inserted into the medical device.

11. The method of using an inserter according to claim 10, wherein the connecting of the liquid injection tool to the tubular portion of the inserter occurs while the tubular portion of the inserter is connected to the first end portion of the tubular holder and while the portion of the medical elongated body is accommodated in the tubular holder.

12. The method of using an inserter according to claim 10, wherein the inserter comprises a connector, the connector having a connector lumen extending through the connector, the tubular portion of the inserter having a main lumen extending through the tubular portion, the connecting of the liquid injection tool to the tubular portion of the inserter comprising connecting one end of the connector and one end of the tubular portion to one another so that the connector lumen and the main lumen are in fluid communication with one another.

13. The method of using an inserter according to claim 10, wherein the connecting of the liquid injection tool to the tubular portion of the inserter comprises connecting an injection tool interlock portion at one end of the inserter to one end of the liquid injection tool, and the supplying of the liquid to the inserter from the liquid injection tool comprises introducing the liquid into the one end of the inserter so that the liquid flows toward an opposite end of the inserter that is connected to the first end portion of the tubular holder.

14. The method of using an inserter according to claim 10, wherein the tubular portion of the inserter has a main lumen that extends between opposite ends of the tubular portion, the connecting of the liquid injection tool to the tubular portion of the inserter comprising connecting the liquid injection tool to an auxiliary tube that is bifurcated from the tubular portion, the auxiliary tube having an auxiliary lumen that fluidly communicates with the main lumen at a position between the opposite ends of the tubular portion.

15. The method of using an inserter according to claim 10, wherein the supplying of the liquid to the inserter occurs before the inserting of the tubular portion of the inserter into the medical device and before the advancing of the medical elongated body relative to the tubular portion of the inserter and relative to the medical device.

16. A method of using an inserter, comprising:

connecting a liquid injection tool to a tubular portion, the tubular portion having a first open end, a second open end that is opposite the first open end, and a main lumen extending between the first and second open ends, the tubular portion having at least a portion of a medical elongated body accommodated in the main lumen, with a first end portion of a tubular holder being connected to the open second open of the tubular portion;

supplying a liquid to the tubular portion from the liquid injection tool while the first end portion of the tubular holder is connected to the open second open of the tubular portion so that: i) the liquid flows into the main lumen in the tubular portion while the portion of the medical elongated body is accommodated in the main lumen; ii) the liquid in the main lumen of the tubular portion flows into the tubular holder while the portion of the medical elongated body is accommodated in the main lumen; and iii) the liquid in the tubular holder is discharged out of the tubular holder to perform priming on the medical elongated body;

connecting the first open end of the tubular portion with a medical device while the portion of the medical elongated body is accommodated in the main lumen of the tubular portion; and advancing the medical elongated body relative to the tubular portion and relative to the medical device to move at least a distal portion of the medical elongated body into the medical device while the tubular portion is connected to the medical device.

17. The method of using an inserter according to claim 16, wherein the supplying of the liquid to the tubular portion occurs before the connecting of the first open end of the tubular portion with the medical device and before the advancing of the medical elongated body relative to the tubular portion inserter and relative to the medical device.

18. The method of using an inserter according to claim 16, wherein the tubular holder includes a second end portion opposite the first end portion, the medical elongated body having a proximal end portion that extends outside the tubular holder at the second end portion of the tubular holder, and wherein the liquid in the tubular holder is discharged out of the tubular holder by way of the second end portion of the tubular holder.

19. The method of using an inserter according to claim 16, wherein the tubular holder includes a second end portion opposite the first end portion, the medical elongated body having a proximal end portion that extends outside the tubular holder at the second end portion of the tubular holder, the advancing of the medical elongated body relative to the tubular portion and relative to the medical device occurring by pushing the proximal end portion of the medical elongated body.

20. The method of using an inserter according to claim 16, further comprising disconnecting the first open end of the tubular portion from the medical device after the moving of the distal portion of the medical elongated body into the medical device.

* * * * *